(12) United States Patent
Chernysh et al.

(10) Patent No.: US 8,372,406 B2
(45) Date of Patent: Feb. 12, 2013

(54) ANTITUMORAL AND ANTIVIRAL PEPTIDES

(75) Inventors: Sergey I. Chernysh, St. Petersburg (RU); German P. Bekker, Moscow (RU)

(73) Assignee: Sergey Chernysh, St. Petersburg (RU)

( * ) Notice: Subject to any disclaimer, the term of this patent is extended or adjusted under 35 U.S.C. 154(b) by 1212 days.

(21) Appl. No.: 10/585,715

(22) PCT Filed: Dec. 30, 2004

(86) PCT No.: PCT/RU2004/000541
§ 371 (c)(1), (2), (4) Date: May 14, 2007

(87) PCT Pub. No.: WO2005/068491
PCT Pub. Date: Jul. 28, 2005

(65) Prior Publication Data
US 2007/0293424 A1    Dec. 20, 2007

(30) Foreign Application Priority Data
Jan. 15, 2004  (RU) .................... 2004100856

(51) Int. Cl.
*A61K 39/38* (2006.01)
*A61K 39/00* (2006.01)
*C07K 7/00* (2006.01)

(52) U.S. Cl. .................. 424/184.1; 424/185.1; 530/300

(58) Field of Classification Search .................. None
See application file for complete search history.

(56) References Cited

U.S. PATENT DOCUMENTS

| | | | | |
|---|---|---|---|---|
| 5,231,081 | A | 7/1993 | Stiefel et al. | 514/6 |
| 5,773,572 | A * | 6/1998 | Fishleigh et al. | 530/324 |
| 2002/0151679 | A1 * | 10/2002 | Kim et al. | 530/327 |
| 2003/0166558 | A1 * | 9/2003 | Frangione et al. | 514/12 |

FOREIGN PATENT DOCUMENTS

| | | |
|---|---|---|
| DE | 197 41 607 A 1 | 3/1999 |
| EP | 1114829 A2 * | 7/2001 |
| EP | 0 668 350 B1 | 7/2004 |
| RU | 2 172 322 C1 | 8/2001 |
| WO | 96/13590 | 5/1996 |
| WO | 00/42071 | 7/2000 |
| WO | 01/77687 | 10/2001 |
| WO | 01/83747 | 11/2001 |
| WO | 03/045128 | 6/2003 |
| WO | 2004/018511 | 3/2004 |
| WO | 2004/085464 | 10/2004 |
| WO | 2006/026977 | 3/2006 |

OTHER PUBLICATIONS

N. I. Perevodchikova, Clinic Chemotherapy of Tumor Diseases—in Russian, Moscow: Medicine, 1979, pp. 100-103.
Zee et al., J. Clin. Oncol., 1998, 16, 8, pp. 2834-2839.
Aviles et al., Leuk. Lymphoma, 1998, 30, 5-6, pp. 651-656 (Abstract).
Gilbert, Cancer, 1998, 83, 6, pp. 1205-1213.
Rutledge, Chin and Schepartz. Current Opinion in Chemical Biology, 2002, 6, pp. 479-485.
S.K. Narula, R. Cofman, eds., New Cytokines as Potential Drugs, Birkhauser Verlag, Basel, 2000, pp. 68-69 and 89-90.
Chernysh et al., Proceedings of National Academy of Science, 2002, 99, pp. 12628-12632.
Kourie, J.I., *Chem. Biol. Interact.*, 2001, 138, 1-26.
Taylor, S.C., Green, K.N., Smith, I.F. & Peers, C. *Am. J. Physiol. Cell Physiol.*, 2001, 281, 1850-1857.
Mabbott, N.A., Brown, K.L., Manson, J. & Bruce, M.E., *Immunology*, 1997, 92, pp. 161-165.
Kawano et al., "Structural Requirements of the N-terminal octapeptide repeat of prion protein", Peptide Science, vol. 2003, Oct. 29, 2003-Oct. 31, 2004, pp. 375-378, XP009092972; Abstract; peptides WGQPH, HGGGQGQP and HGGGQGQPN. (Copy to be provided.).
Database UniProt [online], Feb. 1, 1995, Major prion protein 2 precursor (PrP) (Major scrapie-associated fibril protein 2) (CD230 antigen), XP002460632, retrieved from EBI accession No. UNIPROT:P40243, Database accession No. P40243. (Copy to be provided.).
Supplementary European Search Report for corresponding Application No. PCT/RU2004/000541 mailed Feb. 2, 2008.
Kawano et al., "Structural Requirements of the N-terminal octapeptide repeat of prion protein", Peptide Science, vol. 2003, Oct. 29, 2003-Oct. 31, 2004, pp. 375-378, XP009092972; Abstract; peptides WGQPH, HGGGQGQP and HGGGQGQPN.
Database UniProt [online], Feb. 1, 1995, Major prion protein 2 precursor (PrP) (Major scrapie-associated fibril protein 2) (CD230 antigen), XP002460632, retrieved from EBI accession No. UNIPROT:P40243, Database accession No. P40243.

* cited by examiner

*Primary Examiner* — Vanessa L Ford
*Assistant Examiner* — Sandra Dillahunt
(74) *Attorney, Agent, or Firm* — Renner, Otto, Boisselle & Sklar, LLP

(57) ABSTRACT

The invention relates to novel compositions of general formula (1) consisting of $X_1$ Trp Gly Gln $X_2$ or the pharmaceutically acceptable salts or esters or amides thereof, wherein $X_1$ is absent or contains at least one type of aminoacid, $X_2$ is absent or contains at least one type of aminoacid. The inventive compositions produce an antitumoral and antiviral effect by suppressing a tumoral cells proliferation, potentiating the action of other antitumoral preparations and by stimulating antitumoral and antiviral immunologic mechanisms.

8 Claims, 8 Drawing Sheets

Fig. 1. Final stage of allostatin-1 purification by HPLC method
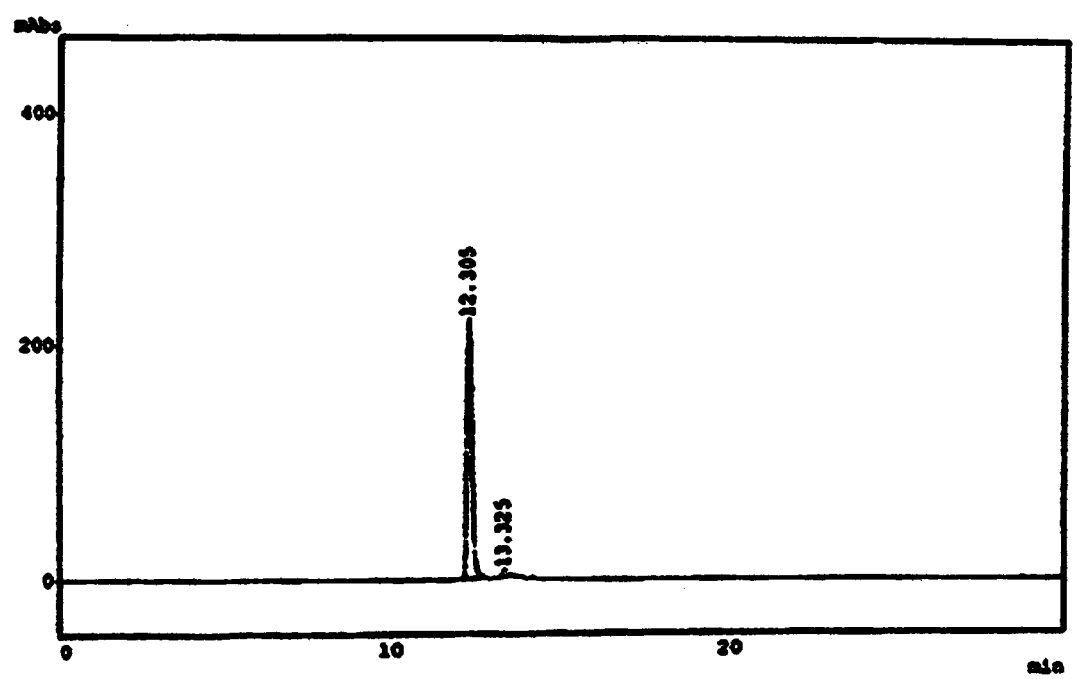

Fig. 2. Mass-spectrum of allostatin-1
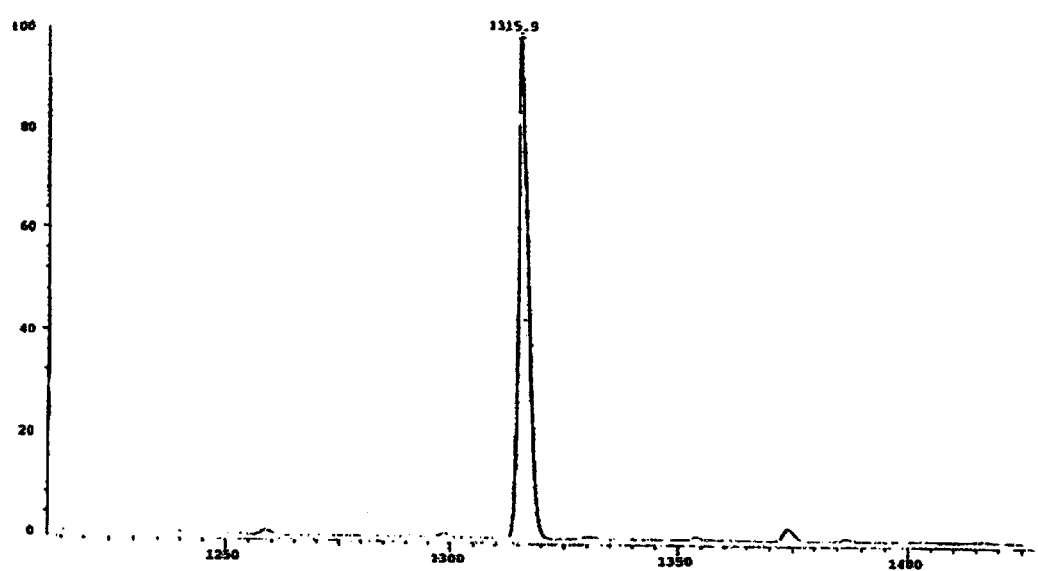

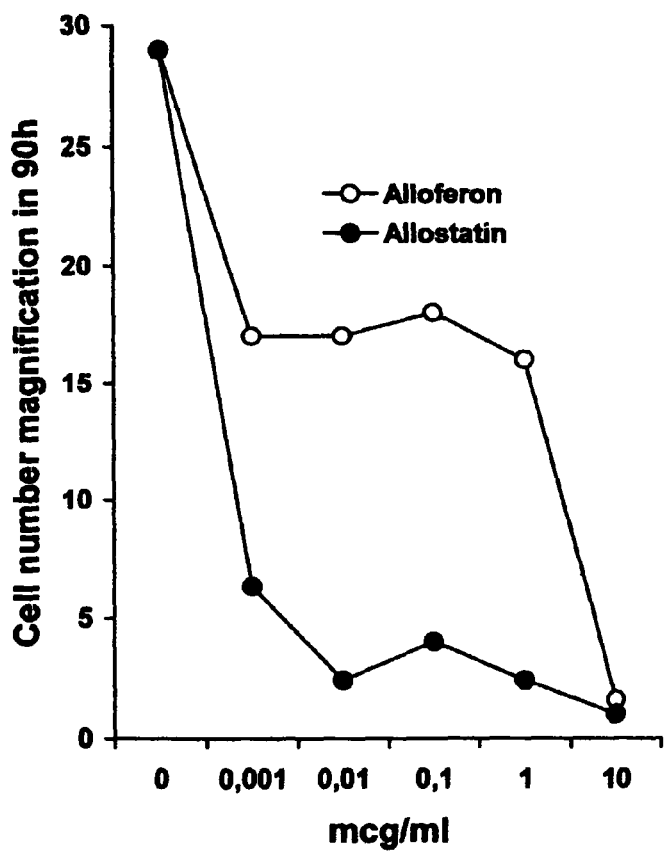
Fig. 3. *In vitro* influence of allostatin and alloferon onto proliferation of tumor cells of P388D1 line.

Fig. 4. Tumor growth suppression of DBA line of mice, implanted by cells of syngenic lymphoid neoplasm R388, after combined administration of cytostatics (chemotherapy) and allostatin.
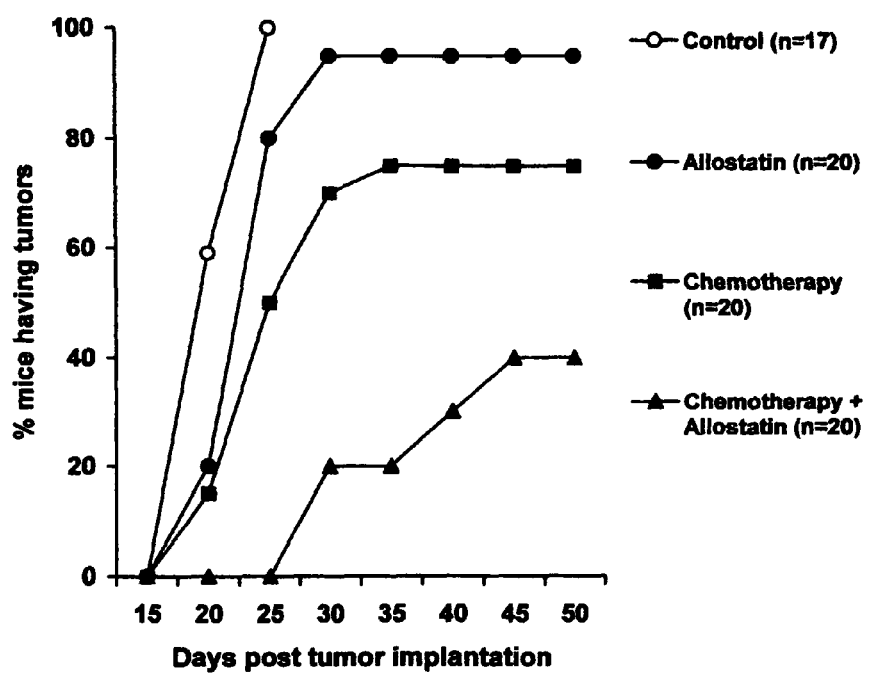

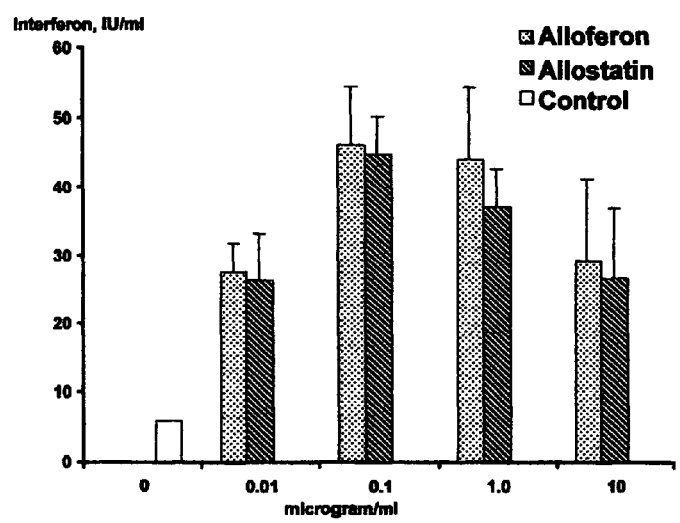
Figure 5. In vitro production of interferon by human leucocytes in the presence of alloferon and allostatin.

Fig. 6
Table 1. Sequence homology of the proposed peptide and prion peptides of mammals.

| | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| SEQ ID NO 1 Allostatin 1 | His | Gly | Val | Ser | Bly | Trp | Gly | Gln | | His | Gly | | Thr | His | Gly |
| SEQ ID NO 2 PrP1 Trast f 80-91 | His | Gly | Gly | | Gly | Trp | Gly | Gln | Pro | His | Gly | | | Gly | Gly |
| SEQ ID NO 3 PrP1 Trast f 96-108 | His | Gly | Gly | Gly | Gly | Trp | Gly | Gln | | Gly | Gly | | Thr | His | Gly |
| SEQ ID NO 4 PrP2 Trast f 64-75 | His | Gly | Gly | | Gly | Trp | Gly | Gln | Pro | His | Val | | | Gly | Gly |
| SEQ ID NO 5 PrP2 Trast F 72-83 | His | Val | Gly | | Gly | Trp | Gly | Gln | Pro | His | Gly | | | Gly | Gly |
| SEQ ID NO 6 PrP2 Trast f 88-100 | His | Gly | Gly | Gly | Gly | Trp | Gly | Gln | | Gly | Gly | | Thr | His | Gly |
| SEQ ID NO 7 Prio bovin f 96-108 | His | Gly | Gly | Gly | Gly | Trp | Gly | Gln | | Gly | Gly | | Thr | His | Gly |
| SEQ ID NO 8 Prio bovin f 64-75 | His | Gly | Gly | | Gly | Trp | Gly | Gln | Pro | His | Gly | | | Gly | Gly |
| SEQ ID NO 9 PrP Human f 52-66 | Gln | Gly | Gly | Gly | Gly | Trp | Gly | Gln | Pro | His | Gly | Gly | Gly | Trp | Gly |
| SEQ ID NO 10 PrP Human f 69-83 | His | Gly | Gly | Gly | | Trp | Gly | Gln | Pro | His | Gly | Gly | Gly | Trp | Gly |
| SEQ ID NO 11 PrP Human f 85-97 | His | Gly | Gly | Gly | | Trp | Gly | Gln | | Gly | Gly | Gly | Thr | His | Ser |
| consensus-sequence | | | | | | Trp | Gly | Gln | | | | | | | |

Fig. 7
Table 2. Comparison of aminoacid sequences of aaloferon-1 and allostatin-1.

| Positions | 1 | 2 | 3 | 4 | 5 | 6 | 7 | 8 | 9 | 10 | 11 | 12 | 13 |
|---|---|---|---|---|---|---|---|---|---|---|---|---|---|
| SEQ ID NO 1 Allostatin 1 | His | Gly | Val | Ser | Gly | Trp | Gly | Gln | His | Gly | Thr | His | Gly |
| SEQ ID NO 2 Alloferon 1 | His | Gly | Val | Ser | Gly | His | Gly | Gln | His | Gly | Val | His | Gly |

Fig. 8

Table 3. Comparison of general structural formula of aaloferon and allostatin.

| Alloferons | $X_1$ | | His | Gly | $X_2$ | His | Gly | Val | $X_3$ |
|---|---|---|---|---|---|---|---|---|---|
| Allostatins | $X_1$ | | Trp | Gly | Gln | $X_2$ | | | |

Fig. 9

Table 4. Combines action of cyclophosphamide and allostatin onto ability of tumor cells of P388D1 line to form daughter clones.

| Preparation | Concentration | Number of clones in a single well | | | Average number of clones |
|---|---|---|---|---|---|
| | | 1 | 2 | 3 | |
| Control | — | 16 | 16 | 12 | 14.7 ± 1.3 |
| Cyclophos-phamid | 1.5 mcg/ml | 12 | 19 | 14 | 15.0 ± 2.1 |
| Allostatin | 0.1 mcg/ml | 21 | 20 | 14 | 18.3 ± 2.2 |
| | 1 mcg/ml | 14 | 19 | 19 | 17.3 ± 1.7 |
| | 10 mcg/ml | 16 | 15 | 21 | 17.3 ± 1.9 |
| Cyclophos-phamid + al-lostatin | 1550 ng/ml + 0.1 mcg/ml | 8 | 8 | 9 | 8.7 ± 0.3 |
| | 1550 ng/ml + 1 mcg/ml | 6 | 6 | 10 | 7.3 ± 1.3 |
| | 1550 ng/ml + 10 mcg/ml | 3 | 4 | 4 | 3.7 ± 0.3 |

Fig. 10

Table 5. Antiviral activity of allostatin and alloferon towards A/Aichi/2/68 (H3N2) influenza virus on the model of lethal influenza infection of white mice.

| Preparation | Virus dosage, $LD_{50}$ | Death-rate of animals (dead/infected, animals) | Percentage of death, % | Death-rate for the sum of two virus does, % |
|---|---|---|---|---|
| Control | 30 | 10/10 | 100 | 90 |
|  | 3 | 8/10 | 80 |  |
| Alloferon | 30 | 6/10 | 60 | 50** |
|  | 3 | 4/10 | 40 |  |
| Allostatin | 30 | 7/10 | 70 | 50** |
|  | 3 | 3/10 | 30 |  |

** Probability of difference from control P<0.01

SEQUENCE LISTING

```
<160> NUMBER OF SEQ ID NOS: 23

<210> SEQ ID NO 1
<211> LENGTH: 13
<212> TYPE: PRT
<213> ORGANISM: Artificial sequence
<220> FEATURE:
<223> OTHER INFORMATION: Synthetic construct designed on the basis of
      the peptides SEQ ID NO 2-12 comparison

<400> SEQUENCE: 1

His Gly Val Ser Gly Trp Gly Gln His Gly Thr His Gly
1               5                   10

<210> SEQ ID NO 2
<211> LENGTH: 264
<212> TYPE: PRT
<213> ORGANISM: Tragelaphus strepsiceros
<220> FEATURE:
<221> NAME/KEY: SITE
<222> LOCATION: (80)..(91)
<223> OTHER INFORMATION: fragment of Trast prion protein 1 precursor
      (PrP1 Trast)
<300> PUBLICATION INFORMATION:
<308> DATABASE ACCESSION NUMBER: Swissprot/P40242
```

-continued

```
<309> DATABASE ENTRY DATE: 1995-02-01
<313> RELEVANT RESIDUES IN SEQ ID NO: (80)..(91)

<400> SEQUENCE: 2
```

Met Val Lys Ser His Ile Gly Ser Trp Ile Leu Val Leu Phe Val Ala
1               5                   10                  15

Met Trp Ser Asp Val Ala Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Ser Gln Gly Gly Gly Trp Gly Gln Pro His
    50                  55                  60

Gly Gly Gly Trp Gly Gln Pro His Gly Gly Trp Gly Gln Pro His
65                  70                  75                  80

Gly Gly Gly Trp Gly Gln Pro His Gly Gly Trp Gly Gln Pro His
                85                  90                  95

Gly Gly Gly Gly Trp Gly Gln Gly Thr His Gly Gln Trp Asn Lys
            100                 105                 110

Pro Ser Lys Pro Lys Thr Asn Met Lys His Val Ala Gly Ala Ala Ala
        115                 120                 125

Ala Gly Ala Val Val Gly Gly Leu Gly Gly Tyr Met Leu Gly Ser Ala
    130                 135                 140

Met Ser Arg Pro Leu Ile His Phe Gly Ser Asp Tyr Glu Asp Arg Tyr
145                 150                 155                 160

Tyr Arg Glu Asn Met Tyr Arg Tyr Pro Asn Gln Val Tyr Tyr Arg Pro
                165                 170                 175

Val Asp Gln Tyr Ser Asn Gln Asn Asn Phe Val His Asp Cys Val Asn
            180                 185                 190

Ile Thr Val Lys Gln His Thr Val Thr Thr Thr Lys Gly Glu Asn
        195                 200                 205

Phe Thr Glu Thr Asp Ile Lys Met Met Glu Arg Val Val Glu Gln Met
    210                 215                 220

Cys Ile Thr Gln Tyr Gln Arg Glu Ser Glu Ala Tyr Tyr Gln Arg Gly
225                 230                 235                 240

Ala Ser Val Ile Leu Phe Ser Ser Pro Pro Val Ile Leu Leu Ile Ser
                245                 250                 255

Phe Leu Ile Phe Leu Ile Val Gly
            260

```
<210> SEQ ID NO 3
<211> LENGTH: 264
<212> TYPE: PRT
<213> ORGANISM: Tragelaphus strepsiceros
<220> FEATURE:
<221> NAME/KEY: SITE
<222> LOCATION: (96)..(108)
<223> OTHER INFORMATION: fragment of Trast prion protein 1 precursor
      (PrP1 Trast)
<300> PUBLICATION INFORMATION:
<308> DATABASE ACCESSION NUMBER: Swissprot/P40242
<309> DATABASE ENTRY DATE: 1995-02-01
<313> RELEVANT RESIDUES IN SEQ ID NO: (96)..(108)

<400> SEQUENCE: 3
```

Met Val Lys Ser His Ile Gly Ser Trp Ile Leu Val Leu Phe Val Ala
1               5                   10                  15

Met Trp Ser Asp Val Ala Leu Cys Lys Lys Arg Pro Lys Pro Gly Gly
            20                  25                  30

Gly Trp Asn Thr Gly Gly Ser Arg Tyr Pro Gly Gln Gly Ser Pro Gly

```
                 35                  40                  45
Gly Asn Arg Tyr Pro Ser Gln Gly Gly Gly Trp Gly Gln Pro His
 50                  55                  60

Gly Gly Gly Trp Gly Gln Pro His Gly Gly Trp Gly Gln Pro His
 65                  70                  75                  80

Gly Gly Gly Trp Gly Gln Pro His Gly Gly Trp Gly Gln Pro His
                     85                  90                  95

Gly Gly Gly Trp Gly Gln Gly Thr His Gly Gln Trp Asn Lys
                100                 105                 110

Pro Ser Lys Pro Lys Thr Asn Met Lys His Val Ala Gly Ala Ala
                115                 120                 125

Ala Gly Ala Val Val Gly Gly Leu Gly Gly Tyr Met Leu Gly Ser Ala
    130                 135                 140

Met Ser Arg Pro Leu Ile His Phe Gly Ser Asp Tyr Glu Asp Arg Tyr
145                 150                 155                 160

Tyr Arg Glu Asn Met Tyr Arg Tyr Pro Asn Gln Val Tyr Tyr Arg Pro
                165                 170                 175

Val Asp Gln Tyr Ser Asn Gln Asn Asn Phe Val His Asp Cys Val Asn
                180                 185                 190

Ile Thr Val Lys Gln His Thr Val Thr Thr Thr Lys Gly Glu Asn
                195                 200                 205

Phe Thr Glu Thr Asp Ile Lys Met Met Glu Arg Val Val Glu Gln Met
210                 215                 220

Cys Ile Thr Gln Tyr Gln Arg Glu Ser Glu Ala Tyr Tyr Gln Arg Gly
225                 230                 235                 240

Ala Ser Val Ile Leu Phe Ser Ser Pro Val Ile Leu Leu Ile Ser
                245                 250                 255

Phe Leu Ile Phe Leu Ile Val Gly
                260

<210> SEQ ID NO 4
<211> LENGTH: 256
<212> TYPE: PRT
<213> ORGANISM: Tragelaphus strepsiceros
<220> FEATURE:
<221> NAME/KEY: SITE
<222> LOCATION: (64)..(75)
<223> OTHER INFORMATION: fragment of Trast prion protein 2 precursor
      (PrP2 Trast)
<300> PUBLICATION INFORMATION:
<308> DATABASE ACCESSION NUMBER: Swissprot/P40243
<309> DATABASE ENTRY DATE: 1995-02-01
<313> RELEVANT RESIDUES IN SEQ ID NO: (64)..(75)

<400> SEQUENCE: 4

Met Val Lys Ser His Ile Gly Ser Trp Ile Leu Val Leu Phe Val Ala
 1               5                  10                  15

Met Trp Ser Asp Val Ala Leu Cys Lys Lys Arg Pro Lys Pro Gly Gly
                20                  25                  30

Gly Trp Asn Thr Gly Gly Ser Arg Tyr Pro Gly Gln Gly Ser Pro Gly
                35                  40                  45

Gly Asn Arg Tyr Pro Pro Gln Glu Gly Gly Asp Trp Gly Gln Pro His
 50                  55                  60

Gly Gly Gly Trp Gly Gln Pro His Val Gly Trp Gly Gln Pro His
 65                  70                  75                  80

Gly Gly Gly Trp Gly Gln Pro His Gly Gly Gly Trp Gly Gln Gly
                 85                  90                  95

Gly Thr His Gly Gln Trp Asn Lys Pro Ser Lys Pro Lys Thr Asn Met
```

```
              100                 105                 110
Lys His Val Ala Gly Ala Ala Ala Gly Ala Val Val Gly Gly Leu
            115                 120                 125

Gly Gly Tyr Met Leu Gly Ser Ala Met Ser Arg Pro Leu Ile His Phe
            130                 135                 140

Gly Ser Asp Tyr Glu Asp Arg Tyr Tyr Arg Glu Asn Met Tyr Arg Tyr
145                 150                 155                 160

Pro Asn Gln Val Tyr Tyr Arg Pro Val Asp Gln Tyr Ser Asn Gln Asn
            165                 170                 175

Asn Phe Val His Asp Cys Val Asn Ile Thr Val Lys Gln His Thr Val
            180                 185                 190

Thr Thr Thr Thr Lys Gly Glu Asn Phe Thr Glu Thr Asp Ile Lys Met
            195                 200                 205

Met Glu Arg Val Val Glu Gln Met Cys Ile Thr Gln Tyr Gln Arg Glu
            210                 215                 220

Ser Glu Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
            245                 250                 255

<210> SEQ ID NO 5
<211> LENGTH: 256
<212> TYPE: PRT
<213> ORGANISM: Tragelaphus strepsiceros
<220> FEATURE:
<221> NAME/KEY: SITE
<222> LOCATION: (72)..(83)
<223> OTHER INFORMATION: fragment of Trast prion protein 2 precursor
      (PrP2 Trast)
<300> PUBLICATION INFORMATION:
<308> DATABASE ACCESSION NUMBER: Swissprot/P40243
<309> DATABASE ENTRY DATE: 1995-02-01
<313> RELEVANT RESIDUES IN SEQ ID NO: (72)..(83)

<400> SEQUENCE: 5

Met Val Lys Ser His Ile Gly Ser Trp Ile Leu Val Leu Phe Val Ala
1               5                   10                  15

Met Trp Ser Asp Val Ala Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
            35                  40                  45

Gly Asn Arg Tyr Pro Pro Gln Glu Gly Gly Asp Trp Gly Gln Pro His
50                  55                  60

Gly Gly Gly Trp Gly Gln Pro His Val Gly Gly Trp Gly Gln Pro His
65                  70                  75                  80

Gly Gly Gly Trp Gly Gln Pro His Gly Gly Gly Trp Gly Gln Gly
            85                  90                  95

Gly Thr His Gly Gln Trp Asn Lys Pro Ser Lys Pro Lys Thr Asn Met
            100                 105                 110

Lys His Val Ala Gly Ala Ala Ala Gly Ala Val Val Gly Gly Leu
            115                 120                 125

Gly Gly Tyr Met Leu Gly Ser Ala Met Ser Arg Pro Leu Ile His Phe
            130                 135                 140

Gly Ser Asp Tyr Glu Asp Arg Tyr Tyr Arg Glu Asn Met Tyr Arg Tyr
145                 150                 155                 160

Pro Asn Gln Val Tyr Tyr Arg Pro Val Asp Gln Tyr Ser Asn Gln Asn
            165                 170                 175

Asn Phe Val His Asp Cys Val Asn Ile Thr Val Lys Gln His Thr Val
```

```
                    180                 185                 190
Thr Thr Thr Thr Lys Gly Glu Asn Phe Thr Glu Thr Asp Ile Lys Met
            195                 200                 205

Met Glu Arg Val Val Glu Gln Met Cys Ile Thr Gln Tyr Gln Arg Glu
        210                 215                 220

Ser Glu Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255

<210> SEQ ID NO 6
<211> LENGTH: 256
<212> TYPE: PRT
<213> ORGANISM: Tragelaphus strepsiceros
<220> FEATURE:
<221> NAME/KEY: SITE
<222> LOCATION: (88)..(100)
<223> OTHER INFORMATION: fragment of Trast prion protein 2 precursor
      (PrP2 Trast)
<300> PUBLICATION INFORMATION:
<308> DATABASE ACCESSION NUMBER: Swissprot/P40243
<309> DATABASE ENTRY DATE: 1995-02-01
<313> RELEVANT RESIDUES IN SEQ ID NO: (88)..(100)

<400> SEQUENCE: 6

Met Val Lys Ser His Ile Gly Ser Trp Ile Leu Val Leu Phe Val Ala
1               5                   10                  15

Met Trp Ser Asp Val Ala Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Glu Gly Gly Asp Trp Gly Gln Pro His
    50                  55                  60

Gly Gly Gly Trp Gly Gln Pro His Val Gly Gly Trp Gly Gln Pro His
65                  70                  75                  80

Gly Gly Gly Trp Gly Gln Pro His Gly Gly Gly Trp Gly Gln Gly
                85                  90                  95

Gly Thr His Gly Gln Trp Asn Lys Pro Ser Lys Pro Lys Thr Asn Met
            100                 105                 110

Lys His Val Ala Gly Ala Ala Ala Gly Ala Val Val Gly Gly Leu
        115                 120                 125

Gly Gly Tyr Met Leu Gly Ser Ala Met Ser Arg Pro Leu Ile His Phe
    130                 135                 140

Gly Ser Asp Tyr Glu Asp Arg Tyr Tyr Arg Glu Asn Met Tyr Arg Tyr
145                 150                 155                 160

Pro Asn Gln Val Tyr Tyr Arg Pro Val Asp Gln Tyr Ser Asn Gln Asn
                165                 170                 175

Asn Phe Val His Asp Cys Val Asn Ile Thr Val Lys Gln His Thr Val
            180                 185                 190

Thr Thr Thr Thr Lys Gly Glu Asn Phe Thr Glu Thr Asp Ile Lys Met
        195                 200                 205

Met Glu Arg Val Val Glu Gln Met Cys Ile Thr Gln Tyr Gln Arg Glu
    210                 215                 220

Ser Glu Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255
```

```
<210> SEQ ID NO 7
<211> LENGTH: 264
<212> TYPE: PRT
<213> ORGANISM: Bos taurus
<220> FEATURE:
<221> NAME/KEY: SITE
<222> LOCATION: (96)..(108)
<223> OTHER INFORMATION: fragment of Bovine prion protein 1 precursor
      (Prio bovin)
<300> PUBLICATION INFORMATION:
<308> DATABASE ACCESSION NUMBER: Swissprot/P10279
<309> DATABASE ENTRY DATE: 1989-03-10
<313> RELEVANT RESIDUES IN SEQ ID NO: (96)..(108)

<400> SEQUENCE: 7

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Trp Gly Gln Pro His
    50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Trp Gly Gln Pro His
                85                  90                  95

Gly Gly Gly Gly Trp Gly Gln Gly Gly Thr His Gly Gln Trp Asn Lys
            100                 105                 110

Pro Ser Lys Pro Lys Thr Asn Met Lys His Val Ala Gly Ala Ala Ala
            115                 120                 125

Ala Gly Ala Val Val Gly Leu Gly Gly Tyr Met Leu Gly Ser Ala
        130                 135                 140

Met Ser Arg Pro Leu Ile His Phe Gly Ser Asp Tyr Glu Asp Arg Tyr
145                 150                 155                 160

Tyr Arg Glu Asn Met His Arg Tyr Pro Asn Gln Val Tyr Tyr Arg Pro
                165                 170                 175

Val Asp Gln Tyr Ser Asn Gln Asn Asn Phe Val His Asp Cys Val Asn
            180                 185                 190

Ile Thr Val Lys Glu His Thr Val Thr Thr Thr Thr Lys Gly Glu Asn
        195                 200                 205

Phe Thr Glu Thr Asp Ile Lys Met Met Glu Arg Val Val Glu Gln Met
210                 215                 220

Cys Ile Thr Gln Tyr Gln Arg Glu Ser Gln Ala Tyr Tyr Gln Arg Gly
225                 230                 235                 240

Ala Ser Val Ile Leu Phe Ser Ser Pro Pro Val Ile Leu Leu Ile Ser
                245                 250                 255

Phe Leu Ile Phe Leu Ile Val Gly
            260

<210> SEQ ID NO 8
<211> LENGTH: 264
<212> TYPE: PRT
<213> ORGANISM: Bos taurus
<220> FEATURE:
<221> NAME/KEY: SITE
<222> LOCATION: (64)..(75)
<223> OTHER INFORMATION: fragment of Bovine prion protein 1 precursor
      (Prio bovin)
<300> PUBLICATION INFORMATION:
<308> DATABASE ACCESSION NUMBER: Swissprot/P10279
<309> DATABASE ENTRY DATE: 1989-03-10
```

-continued

<313> RELEVANT RESIDUES IN SEQ ID NO: (64)..(75)

<400> SEQUENCE: 8

```
Met Val Lys Ser His Ile Gly Ser Trp Ile Leu Val Leu Phe Val Ala
1               5                   10                  15
Met Trp Ser Asp Val Gly Leu Cys Lys Lys Arg Pro Lys Pro Gly Gly
            20                  25                  30
Gly Trp Asn Thr Gly Gly Ser Arg Tyr Pro Gly Gln Gly Ser Pro Gly
        35                  40                  45
Gly Asn Arg Tyr Pro Pro Gln Gly Gly Gly Trp Gly Gln Pro His
    50                  55                  60
Gly Gly Gly Trp Gly Gln Pro His Gly Gly Gly Trp Gly Gln Pro His
65                  70                  75                  80
Gly Gly Gly Trp Gly Gln Pro His Gly Gly Gly Trp Gly Gln Pro His
                85                  90                  95
Gly Gly Gly Gly Trp Gly Gln Gly Gly Thr His Gly Gln Trp Asn Lys
            100                 105                 110
Pro Ser Lys Pro Lys Thr Asn Met Lys His Val Ala Gly Ala Ala Ala
        115                 120                 125
Ala Gly Ala Val Val Gly Gly Leu Gly Gly Tyr Met Leu Gly Ser Ala
    130                 135                 140
Met Ser Arg Pro Leu Ile His Phe Gly Ser Asp Tyr Glu Asp Arg Tyr
145                 150                 155                 160
Tyr Arg Glu Asn Met His Arg Tyr Pro Asn Gln Val Tyr Tyr Arg Pro
                165                 170                 175
Val Asp Gln Tyr Ser Asn Gln Asn Phe Val His Asp Cys Val Asn
            180                 185                 190
Ile Thr Val Lys Glu His Thr Val Thr Thr Thr Thr Lys Gly Glu Asn
        195                 200                 205
Phe Thr Glu Thr Asp Ile Lys Met Met Glu Arg Val Val Glu Gln Met
    210                 215                 220
Cys Ile Thr Gln Tyr Gln Arg Glu Ser Gln Ala Tyr Tyr Gln Arg Gly
225                 230                 235                 240
Ala Ser Val Ile Leu Phe Ser Ser Pro Pro Val Ile Leu Leu Ile Ser
                245                 250                 255
Phe Leu Ile Phe Leu Ile Val Gly
            260
```

<210> SEQ ID NO 9
<211> LENGTH: 253
<212> TYPE: PRT
<213> ORGANISM: Homo sapiens
<220> FEATURE:
<221> NAME/KEY: SITE
<222> LOCATION: (52)..(66)
<223> OTHER INFORMATION: fragment of human prion protein precursor (PrP Human)
<300> PUBLICATION INFORMATION:
<308> DATABASE ACCESSION NUMBER: Swissprot/P04156
<309> DATABASE ENTRY DATE: 1986-11-01
<313> RELEVANT RESIDUES IN SEQ ID NO: (52)..(66)

<400> SEQUENCE: 9

```
Met Ala Asn Leu Gly Cys Trp Met Leu Val Leu Phe Val Ala Thr Trp
1               5                   10                  15
Ser Asp Leu Gly Leu Cys Lys Lys Arg Pro Lys Pro Gly Gly Trp Asn
            20                  25                  30
Thr Gly Gly Ser Arg Tyr Pro Gly Gln Gly Ser Pro Gly Gly Asn Arg
        35                  40                  45
```

```
            Tyr Pro Pro Gln Gly Gly Gly Trp Gly Gln Pro His Gly Gly Gly
                50                  55                  60
            Trp Gly Gln Pro His Gly Gly Trp Gly Gln Pro His Gly Gly
             65                  70                  75                  80
            Trp Gly Gln Pro His Gly Gly Trp Gly Gln Gly Gly Thr His
                                 85                  90                  95
            Ser Gln Trp Asn Lys Pro Ser Lys Pro Lys Thr Asn Met Lys His Met
                            100                 105                 110
            Ala Gly Ala Ala Ala Ala Gly Ala Val Val Gly Gly Leu Gly Gly Tyr
                        115                 120                 125
            Met Leu Gly Ser Ala Met Ser Arg Pro Ile Ile His Phe Gly Ser Asp
                    130                 135                 140
            Tyr Glu Asp Arg Tyr Tyr Arg Glu Asn Met His Arg Tyr Pro Asn Gln
            145                 150                 155                 160
            Val Tyr Tyr Arg Pro Met Asp Glu Tyr Ser Asn Gln Asn Asn Phe Val
                            165                 170                 175
            His Asp Cys Val Asn Ile Thr Ile Lys Gln His Thr Val Thr Thr Thr
                        180                 185                 190
            Thr Lys Gly Glu Asn Phe Thr Glu Thr Asp Val Lys Met Met Glu Arg
                    195                 200                 205
            Val Val Glu Gln Met Cys Ile Thr Gln Tyr Glu Arg Glu Ser Gln Ala
            210                 215                 220
            Tyr Tyr Gln Arg Gly Ser Ser Met Val Leu Phe Ser Ser Pro Pro Val
            225                 230                 235                 240
            Ile Leu Leu Ile Ser Phe Leu Ile Phe Leu Ile Val Gly
                            245                 250

<210> SEQ ID NO 10
<211> LENGTH: 253
<212> TYPE: PRT
<213> ORGANISM: Homo sapiens
<220> FEATURE:
<221> NAME/KEY: SITE
<222> LOCATION: (69)..(83)
<223> OTHER INFORMATION: fragment of human prion protein precursor (PrP
      Human)
<300> PUBLICATION INFORMATION:
<308> DATABASE ACCESSION NUMBER: Swissprot/P04156
<309> DATABASE ENTRY DATE: 1986-11-01
<313> RELEVANT RESIDUES IN SEQ ID NO: (69)..(83)

<400> SEQUENCE: 10

Met Ala Asn Leu Gly Cys Trp Met Leu Val Leu Phe Val Ala Thr Trp
            1               5                   10                  15
            Ser Asp Leu Gly Leu Cys Lys Lys Arg Pro Lys Pro Gly Gly Trp Asn
                            20                  25                  30
            Thr Gly Gly Ser Arg Tyr Pro Gly Gln Gly Ser Pro Gly Gly Asn Arg
                        35                  40                  45
            Tyr Pro Pro Gln Gly Gly Gly Trp Gly Gln Pro His Gly Gly Gly
                50                  55                  60
            Trp Gly Gln Pro His Gly Gly Trp Gly Gln Pro His Gly Gly
             65                  70                  75                  80
            Trp Gly Gln Pro His Gly Gly Trp Gly Gln Gly Gly Thr His
                                 85                  90                  95
            Ser Gln Trp Asn Lys Pro Ser Lys Pro Lys Thr Asn Met Lys His Met
                            100                 105                 110
            Ala Gly Ala Ala Ala Ala Gly Ala Val Val Gly Gly Leu Gly Gly Tyr
                        115                 120                 125
```

```
Met Leu Gly Ser Ala Met Ser Arg Pro Ile Ile His Phe Gly Ser Asp
        130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Arg Glu Ser Gln Ala
        210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250

<210> SEQ ID NO 11
<211> LENGTH: 253
<212> TYPE: PRT
<213> ORGANISM: Homo sapiens
<220> FEATURE:
<221> NAME/KEY: SITE
<222> LOCATION: (85)..(97)
<223> OTHER INFORMATION: fragment of human prion protein precursor (PrP
      Human)
<300> PUBLICATION INFORMATION:
<308> DATABASE ACCESSION NUMBER: Swissprot/P04156
<309> DATABASE ENTRY DATE: 1986-11-01
<313> RELEVANT RESIDUES IN SEQ ID NO: (85)..(97)

<400> SEQUENCE: 11

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
                20                  25                  30

Thr Gly Gly Ser Arg Tyr Pro Gly Gln Gly Ser Pro Gly Gly Asn Arg
            35                  40                  45

Tyr Pro Pro Gln Gly Gly Gly Trp Gly Gln Pro His Gly Gly Gly
    50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
                85                  90                  95

Ser Gln Trp Asn Lys Pro Ser Lys Pro Lys Thr Asn Met Lys His Met
                100                 105                 110

Ala Gly Ala Ala Ala Ala Gly Ala Val Val Gly Gly Leu Gly Gly Tyr
            115                 120                 125

Met Leu Gly Ser Ala Met Ser Arg Pro Ile Ile His Phe Gly Ser Asp
        130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205
```

```
Val Val Glu Gln Met Cys Ile Thr Gln Tyr Glu Arg Glu Ser Gln Ala
    210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250

<210> SEQ ID NO 12
<211> LENGTH: 13
<212> TYPE: PRT
<213> ORGANISM: Calliphora vicina
<220> FEATURE:
<223> OTHER INFORMATION: Alloferon-1
<300> PUBLICATION INFORMATION:
<308> DATABASE ACCESSION NUMBER: Swissprot/P83412
<309> DATABASE ENTRY DATE: 2003-06-27
<313> RELEVANT RESIDUES IN SEQ ID NO: (1)..(13)

<400> SEQUENCE: 12

His Gly Val Ser Gly His Gly Gln His Gly Val His Gly
1               5                   10

<210> SEQ ID NO 13
<211> LENGTH: 5
<212> TYPE: PRT
<213> ORGANISM: Artificial sequence
<220> FEATURE:
<223> OTHER INFORMATION: fragment of peptide SEQ ID NO 1

<400> SEQUENCE: 13

His Gly Val Ser Gly
1               5

<210> SEQ ID NO 14
<211> LENGTH: 4
<212> TYPE: PRT
<213> ORGANISM: Tragelaphus strepsiceros, Bos taurus, Homo sapiens
<220> FEATURE:
<221> NAME/KEY: SITE
<222> LOCATION: (1)..(4)
<223> OTHER INFORMATION: fragment of peptides SEQ ID NO 2, 4, 8, 10, 11

<400> SEQUENCE: 14

His Gly Gly Gly
1

<210> SEQ ID NO 15
<211> LENGTH: 4
<212> TYPE: PRT
<213> ORGANISM: Tragelaphus strepsiceros
<220> FEATURE:
<221> NAME/KEY: SITE
<222> LOCATION: (1)..(4)
<223> OTHER INFORMATION: fragment of peptide SEQ ID NO 5

<400> SEQUENCE: 15

His Val Gly Gly
1

<210> SEQ ID NO 16
<211> LENGTH: 5
<212> TYPE: PRT
<213> ORGANISM: Tragelaphus strepsiceros, Bos taurus
<220> FEATURE:
<221> NAME/KEY: SITE
<222> LOCATION: (1)..(5)
<223> OTHER INFORMATION: fragment of peptide SEQ ID NO 3, 7
```

```
<400> SEQUENCE: 16

His Gly Gly Gly Gly
1               5

<210> SEQ ID NO 17
<211> LENGTH: 5
<212> TYPE: PRT
<213> ORGANISM: Homo sapiens
<220> FEATURE:
<221> NAME/KEY: SITE
<222> LOCATION: (1)..(5)
<223> OTHER INFORMATION: fragment peptide SEQ ID NO 9

<400> SEQUENCE: 17

Gln Gly Gly Gly Gly
1               5

<210> SEQ ID NO 18
<211> LENGTH: 5
<212> TYPE: PRT
<213> ORGANISM: Artificial sequence
<220> FEATURE:
<221> NAME/KEY: SITE
<222> LOCATION: (9)..(13)
<223> OTHER INFORMATION: fragment of peptide SEQ ID NO 1

<400> SEQUENCE: 18

His Gly Thr His Gly
1               5

<210> SEQ ID NO 19
<211> LENGTH: 5
<212> TYPE: PRT
<213> ORGANISM: Tragelaphus strepsiceros
<220> FEATURE:
<221> NAME/KEY: SITE
<222> LOCATION: (9)..(13)
<223> OTHER INFORMATION: fragment of peptide SEQ ID NO 3

<400> SEQUENCE: 19

Gly Gly Thr His Gly
1               5

<210> SEQ ID NO 20
<211> LENGTH: 5
<212> TYPE: PRT
<213> ORGANISM: Tragelaphus strepsiceros
<220> FEATURE:
<221> NAME/KEY: SITE
<222> LOCATION: (8)..(12)
<223> OTHER INFORMATION: fragment of peptide SEQ ID NO 4

<400> SEQUENCE: 20

Gly Gly Thr His Gly
1               5

<210> SEQ ID NO 21
<211> LENGTH: 5
<212> TYPE: PRT
<213> ORGANISM: Tragelaphus strepsiceros, Bos taurus
<220> FEATURE:
<221> NAME/KEY: SITE
<222> LOCATION: (8)..(12)
<223> OTHER INFORMATION: fragment of peptide SEQ ID NO 2, 5, 8

<400> SEQUENCE: 21

Pro His Gly Gly Gly
1               5
```

```
<210> SEQ ID NO 22
<211> LENGTH: 7
<212> TYPE: PRT
<213> ORGANISM: Homo sapiens
<220> FEATURE:
<221> NAME/KEY: SITE
<222> LOCATION: (9)..(15)
<223> OTHER INFORMATION: fragment of peptide SEQ ID NO 9, 10

<400> SEQUENCE: 22

Pro His Gly Gly Gly Trp Gly
1               5

<210> SEQ ID NO 23
<211> LENGTH: 6
<212> TYPE: PRT
<213> ORGANISM: Homo sapiens
<220> FEATURE:
<221> NAME/KEY: SITE
<222> LOCATION: (8)..(13)
<223> OTHER INFORMATION: fragment of peptide SEQ ID NO 11

<400> SEQUENCE: 23

Gly Gly Gly Thr His Ser
1               5
```

ANTITUMORAL AND ANTIVIRAL PEPTIDES

This application is a national phase of International Application No. PCT/RU2004/000541 filed Dec. 30, 2004.

FIELD OF THE INVENTION

The proposed invention relates to proteins and peptides exhibiting antitumoral and antiviral properties, as well as to drugs based thereon.

BACKGROUND OF THE INVENTION

Known are antitumoral peptides of bleomycine group (1). Bleomycines provide a direct cytotoxic action on tumor cells, however, the possibility of their clinic use is restricted by pronounced side effects, first of all onto lungs and kidneys.

Known is use of recombinant proteins of interferon group as activators of antitumoral immunity and inhibitors of tumor cell proliferation. Interferons are used for treating the multiple myeloma (2), Hodgkin's disease (3), myeloid leukemia (4). However, high cost of interferons makes them inaccessible for wide clinical use. Another limitations are side effects associated with possible pyrogenecity, immunogenicity and other undesirable properties of recombinant interferon.

Known are suggestions to use peptide inducers of apoptosis as potential antitumoral drugs (5). However, clinical trends of this direction are still unexplored. Currently, several cytokine-type protein compounds are on the stage of development and clinical testing as antitumoral remedies (6). The most prominent is the use of interleukin-2, but high cost and toxicity of the recombinant interleukin-2 limit its wide use in oncology practice.

Known are suggestions to use hemocyanin and arylphorin proteins as activators of immune response and antitumoral agents (7).

In spite of presence of aforementioned and other elaborations described in the literature, a therapy of oncological diseases remains still ineffective and is practically always highly toxic and expensive. Therefore, searches of new approaches to tumor therapy remain still one of the most important problems of modern medicine.

Alloferons are known as immunomodulating peptides (8). Therapy of viral infections is the main field of use of said alloferons. At the same time, antitumoral properties of said alloferons based upon activation of antitumoral immunity mechanisms, namely interferons and natural killer cells, are known (9). Alloferons are the closest analogues of the present invention in their chemical structure and action mechanism.

SUMMARY OF THE INVENTION

Experimental research of the antitumoral activity of the alloferon has revealed that said peptide depresses the growth of mice tumor syngeneic graft, and thereby it can be attributed to promising antitumoral agents. Effect of alloferon is realized at the level of systemic response of organism onto the grafted tumor. At the same time, an effect of alloferon onto tumor proliferation at the cell level seems to be more complicated. Particularly, in vitro experiments have shown that the alloferon, depending on its concentration in cultural media, may both inhibit (at high concentrations) and stimulate (at low concentrations) proliferation of tumor cells. Presence of growth-stimulating activity restricts the possibility of use the alloferon for tumor therapy, where depressing of malignizated cell proliferation is the main object of the treatment.

The object of the present invention is to provide drugs exhibiting a reduced growth-stimulating activity and enhanced anti-proliferational and cytotoxic activities towards tumor cells, while keeping the immunomodulating mechanism of alloferon effect.

For this purpose, a new family of peptides was developed, which peptides differ from alloferon and other bioactive compounds in their structure, mechanism of action, and therapeutic effect being achieved.

BRIEF DESCRIPTION OF THE DRAWINGS

FIG. 1 is a chromatograph showing the final stage of allostatin-1 purification by HPLC method.

FIG. 2 is a mass spectrum of allostatin-1.

FIG. 3 is a graph showing the in vitro influence of allostatin and alloferon on growth dynamics of tumor cells of P388D1 line.

FIG. 4 is a graph showing tumor growth suppression of DBA line of mice, implanted by cells of syngenic lymphoid neoplasm R388, after combined administration of cytostatics and allostatin.

FIG. 5 is a bar graph showing in vitro production of interferon by human leucocytes in the presence of alloferon and allostatin.

FIG. 6 is a table (Table 1) of the sequence homology of the proposed peptide and prion peptides of mammals.

FIG. 7 is a table (Table 2) of the comparison of amino acid sequences of alloferon-1 and allostatin-1.

FIG. 8 is a table (Table 3) of the comparison of the general structural formula of alloferon and allostatin.

FIG. 9 is a table (Table 4) of the combined action of cyclophosamide and allostatin on the ability of tumor cells of P388D1 line to form daughter clones.

FIG. 10 is a table (Table 5) of the antiviral activity of allostatin and alloferon toward A/Aichi/2/68 (H3N2) influenza virus on the model of lethal influenza infection of white mice.

The claimed group of compounds relates to linear peptides which structure is represented by the following formula:

$$X_1 \text{ Trp Gly Gln } X_2 \tag{1}$$

wherein $X_1$ is absent, or comprises no less than 1 amino acid, $X_2$ is absent, or comprises no less than 1 amino acid.

When developing the present invention, peptide allostatin-1 (SEQ ID NO 1) presented in Table 1 was used as a basic structure. Allostatin-1 has been synthesized by solid-phase synthesis technique and used for studies of biological and therapeutic activity of proposed peptides. Results of the studies are summarized in following examples. The studies have revealed that said peptide has antitumoral activity based on the direct suppression of proliferation of tumor cells and reinforcement of certain links of antitumoral immunity.

During computer analysis of databases containing peptide structures and properties it has been determined that said compound relates to a new family of bioactive peptides previously unknown. Original structure of the proposed peptides ensures the achievement of a new technical level, the possibility of effective suppression of tumor growth and treatment of oncological diseases thereupon.

Analysis of homology of allostatin-1 amino acid sequences and known peptides and proteins, carried out using BLAST SEARCH program upon the data of SWISSPROT database, has revealed several structural analogues of the proposed peptides. These data are summarized in the Table 1.

Revealed sequences with high homology level relative to the allosattin-1, from the structure, functions and origen point of view, belong to prion proteins (PrP), i.e., compounds of a similar group. Prion proteins (prions) are produced by cells of different tissues of many kinds of animals, including human and other mammals. Normal functions of prions are still not sufficiently explored. At the same time it is known that under certain conditions prions can undergo the conformational changes, resulting in pathological scrapie-isoform which is responsible for propagation of some neurodegenerating diseases. Usually, mature prion protein comprises more than 200 amino acid residues. Pathological properties of prions are connected with fragments homologous to 114-134 PrP I fragment of a bull (SEQ ID NO 8), particularly to amyloid hydrophobic region 124-131 (Ala-Gly-Ala-Ala-Ala-Ala-Gly-Ala) of said fragment of sequence SEQ ID NO 8 (10). Allostatin-1 (SEQ ID NO 1) is homologous to repeated sites 64-75, 72-83, 80-91, 87-98, 96-108 of SEQ ID NO 8 but structurally it is completely distinguishing from the site 114-134 PrP I of SEQ ID NO 8. Close structural similarity between said sites and proposed peptides (e.g., 11 of 13 aminoacids (84%) of 96-108 PrP I (SEQ ID NO 8) site of a bull are similar to allostatin SEQ ID NO 1 assumes also the similarity of biological activity. Thus, very probably, one can suppose that fragments of mammal prions homologous to proposed antitumoral peptides, exhibit also similar type of antitumoral activity. Mechanism of probable antitumoral action of said fragments is unknown but some facts suggest that said prions pertain to regulation of T-lymphocytes' activity (11). In turn, T-lymphocytes play the main part in reactions of antitumoral immunity.

Structural and functional similarity to fragments of mammal prions allows to pick out potentially variable sites of the sequence of proposed peptides, in which sites the substitution in composition and ordering of amino acids will not effect essentially onto functional properties of the molecule as a whole. Taking into account the distribution of variable and conservative sites of amino acid sequences shown in the Table 1, the general structural formula (I) includes two variable zones $X_1$ and $X_2$ divided by conservative sequence of tryptophan, glycine and glutamine amino acids (Trp-Gly-Gln). Variable site $X_1$ is absent or it can comprise up to 5 aminoacids or more. Variable region. $X_2$ is absent, or it can comprise up to 7 amino acids or more. Here, the proposed peptides may be included as a functional part of other proteins and polypeptides into larger amino acid sequences, e.g., prion proteins having chain length of 250-300 amino acids.

Compounds of the proposed structure, which are represented by allostatin-1, are synthesized by solid-phase synthesis technique and characterized by HPLC and mass-spectrometry. Said compounds can be obtained in a form of ethers, salts, amides or other pharmaceutically acceptable derivatives. Besides the chemical way of synthesis, proposed peptides can be obtained by genetic engineering techniques or recovered from natural sources.

Other structural analogues of the proposed peptides are alloferons, which have general structural formula described in the patent (12). Results of comparative analysis of structural formulae of alloferons and proposed peptides, allostatins, are presented in the Table 2 and Table 3. Table 2 compares structures of two typical representatives of peptide family, alloferon-1 (SEQ ID NO 12) and allostatin-1 (SEQ ID NO 1). Based on the comparison one can see that said peptides differ from each other in amino acids in positions 6 and 11, namely histidine and valine of alloferon-1, and tryptophan and threonine of allostatin-1, respectively. According to RU 2172322, positions 6 and 11 are invariable part and typical feature of all alloferons. Replacement of amino acids in these positions with tryptophan and threonine results in desired modification of biological activity and therapeutic effect, as following examples confirm.

Comparison of general structural formulae (Table 3) shows that the compositions of conservative sites and arrangement of variable sites of allostatin and alloferon molecules have a qualitative difference. For this reason, they can be rated as two different peptide families.

EXAMPLES CONFIRMING THE POSSIBILITY FOR REALIZATION OF THE INVENTION

Example 1

Allostatin-1 Synthesis

Peptide consisting of 13 aminoacids corresponding to the allostatin-1 structure, was synthesized by solid-phase synthesis technique using the automatic multi-channel synthesizer Multisyntech GmbH Witten and Fmoc-(N-[9-fluorenyl]methoxycarbonyl)-substituted amino acids. Purification of the synthesized peptide was carried out by technique of reversed-phase HPLC using Shimazu LC8 chromatograph equipped with 10 mm Chromasil C18 column. Purity of thus obtained peptide was also controlled by HPLC method (FIG. 1). Correctness of the synthesis is confirmed by MALDI-TOF mass-spectroscopy method using Finnigan TSQ 7000 device (FIG. 2). Mass of the peptide established experimentally corresponds to the calculated one, and deviations are within the range of measurement error.

Example 2

In vitro Influence of Allostatin on Tumor Cells Proliferation

Object of instant experiments is the comparative analysis of influence of allostatin and alloferon on tumor cells proliferation. Effects of allostatin-1 and alloferon-1 in concentrations 0.001, 0.01, 0.1, 1, and 10 microgram per ml on proliferative activity in a mass culture of R388D1-type tumor cells were compared. 5000 cells suspended in 2 ml of RPMI 164 medium were seed into wells of 24-socket plates. Medium used for the experiments comprises 5% fetal calf serum produced by firm "Biolot". Preparations were introduced into wells in 0.2 ml of the sane medium immediately after inoculation, and, in control, equivalent amount of the medium was introduced without medications. Number of cells in 1 ml of incubating medium was estimated by means of hemocytometric camera. Average number of cells in 1 ml of incubating medium after 21, 44, 99 and 144 hours after beginning of the experiment was estimated on the base of 3 independent measurements.

FIG. 3 presents a typical view of allostatin and alloferon influence on growth dynamics of tumor cell population. As an evaluation indicator of anti-proliferative activity of the medication, the value of a growth multiplicity of the population for 90 hours was selected, which value is determined as a ratio of a number of cells in a well in the beginning and at the end of the incubation time. During said period, control number of cells increased approximately 30 times. When medications were used, number of cells and rate of proliferation, respectively, were decreased in a dose-dependent manner. Here, anti-proliferative activity of allostatin 3-7 times exceeds the one of alloferon when concentrations of 0.001-1 mkg/ml were used. Allostatin in a concentration of 10 microgram/ml has almost completely stopped the growth of the tumor cell population over the observation period.

Thus, this example 2 demonstrates the presence of antiproliferative activity of allostatin, and its advantage in comparison with alloferon.

Example 3

In vitro Interaction of Allostatin and Antitumoral Cytostatics

Example 3 shows materials that demonstrate an interaction of allostatin and typical cytostatic, cyclophosphamide, regarding suppression of clonogenic activity of tumor cells. Clonogenic activity index allows to determine the part of tumor cells from general pool which are able to produce viable clones and thus take part in growth and proliferation of the tumor. The main purpose of chemotherapy is a destruction of such actively proliferating cells.

Experimental technique can be summarized as following. Cells of lymphoid neoplasm of a mouse (line R388D1) were cultivated in RPMI 1640 medium containing glutamine, gentamicin and 10% of embryonic calf serum "High clone". 100 R388D1 cells in 1 ml of said medium were seed into each well of 24-socket culture plates. After that, 0.1 ml of the medium with or without testing preparation (control wells) was introduced into each well. Each embodiment of the experiment was independently repeated for 3 times. Numbers of clones were counted after 7 days from the cultivation beginning.

As one can see (Table 4), about 15% of tumor cells resulted in viable clones under conditions of this experiment. Neither cyclophosphamide, nor allostatin taken separately, had a significant influence upon the cloning process. At the same time, their combination has significantly decreased a clonogenic activity of tumor cells, proportionally to allostatin dose.

The present example shows that allostatin has perspectives for use in combined tumor chemotherapy in combination with cytostatics of cyclophosphamide type.

Example 4

Antitumoral Action of Allostatin onto Models of Transplanted Tumors in Mice Each of laboratory mouse (line DBA-1) was subcutaneously injected by 3000 tumor cells of the syngeneic line R388D1. Next day mice were separated into 4 experimental groups. Mice of the first group have got only allostatin in a subcutaneous way in a dosage on 25 microgram at 4, 11 and 18 day after tumor cell transplantation. Second group has got a combination of cytostatic agents, cyclophosphamide (0.56 mg), doxorubicine (0.036 mg) and vincrystine (1.05 microgram) on the day of transplantation and after 7, 14 and 21 days. Third group has got allostatin and combination of cytostatic agents in the same way. Mice of the fourth group (control group) were injected by the solvent (0.9% NaCl) in the same days.

In the control group palpable tumors in grafted areas became apparent after 20 days, after 25 days all mice have had typical subcutaneous tumors of 5-26 mm in a diameter (FIG. 4). In groups where mice have got allostatin or cytostatics separately, tumors were formed after some delays, and moderate part of animals has not exhibited tumor formation during observation time. At the same time, strong and in the most cases irreversible antitumoral action was detected when combination of allostatin and cytostatics was used. Only 40% of mice of this group have exhibited formed tumors during observation period ($P<0.001$ with respect to the control group, and $P<0.05$ with respect to the group administered cytostatics only).

This example, as the Example 3 above, indicates that the allostatin have a pronounced antitumoral effect when it is used in the combination with typical drugs for chemotherapy, widely applied for treating leucosis and other oncological diseases.

Example 5

Immunomodulating (Interferonogenic) Activity of Allostatin

Action mechanism of immunomodulators, which alloferon belongs to, is associated with induction of interferon synthesis provided by blood leucocytes (Chernysh et al., Proceedings of National Academy of Science, 2002, 99, p. 12628-12632). One of the purposes of present invention was to keep immunomodulating action of allostatins in the range of biological activity thereof. The present example illustrates an immunomodulating activity of allostatin-1 using a model of interferon in vitro synthesis provided by leucocytes of a human.

Samples of donated blood were mixed with an aqueous solution of testing sample and culture medium in the ratio of 1:1:8. Final concentration of samples in incubation mixture was 0 (control), 0.01, 0.1, 1, or 10 microgram/ml, for different embodiments of the example. This mixture was incubated at 37° C. for 24 hours in a $CO_2$-thermostat. Then, blood cells were precipitated by centrifugation. After that, serial dilutions of the obtained supernatant were placed into wells of 96-socket plates, covered by monolayer of a test-culture of L-41 cells, and then incubated for 24 hours under the same conditions. Then, the cell monolayer was infected by vesicular stomatitis virus in a dose equal to 100 $LD_{50}$ (dose caused in 50% death of monolayer cells) and incubated at 37° C. for 18 hours. Then, cells were visualized by 0.1% solution of a crystal-purple dye. Part of monolayer destroyed by the virus was determined using measurements of optical density of extracted dye at the wavelength of 590 nm. Values thus obtained were compared with an effect of reference sample of alpha-interferon, and obtained titer of interferon was calculated in IU-units of antiviral activity of alpha-interferon. Results of studies of 6 donated blood samples taken at two analytical repetitions (12 measurements for each point), are summarized in FIG. 5.

The obtained results indicate that interferonogenic activities of allostatin and alloferon have no significant difference. Hence, allostatin acquires specific properties which are suitable to use it as an antitumoral agent, and at the same time, allostatin keeps the immunomodulating activity intrinsic to alloferon. Thus, allostatin can be used in oncology (and in other fields of use) as a dual-purpose drug, both direct (cytotoxic and antiproliferative effects, potentiating of cytostatics' effect) and indirect (immunomodulating) actions.

Example 6

Antiviral Activity of Allostatin

Lethal influenza virus infection of wild-type white mice (body mass of 14-16 g) of both sexes was used as a model in the studies of antiviral action of allostatin. Influenza virus A/Aichi/2/68 (H3N2) adapted to white mice was used in the present study. Allostatin and alloferon were dissolved in distilled water and then 0.25 ml was subcutaneously injected to each animal on the basis of 25 microgram per mouse (1.5 mg/kg of a body). Distilled water was used as a placebo in the control group. Preventive scheme of injection was used to determine the antiviral activity of drugs: single injection of the drug was done 24 hours before infection. Virus doses of 3 and 30 $LD_{50}$ were introduced intranasally into animals under light ether anesthesia. Each testing group comprised of 10 mice. Observation of animals lasted during 14 days. Death-rate of the animals was registered both for experimental and control groups. Results of the experiment are presented in a Table 5. Both of drugs provided similar effective protection against lethal influenza virus infection of mice.

Thus, allostatin keeps an antiviral activity typical for alloferon. One can suppose thereupon that allostatin can be used as antiviral drug, as well as alloferon. The most advisable use thereof is the use instead of alloferon in border-line cases of viral and oncological pathology, e.g. in the case of tumors of viral ethiology or for the purpose of treating viral infections of cancer patients.

REFERENCE

1. N. I. Perevodchikova, Clinic chemotherapy of tumor diseases—*in Russian*, Moscow: Medicine, 1976, pp. 100-103
2. Zee et al., J. Clin. Oncol., 1998, 16, 8, p. 2834-2839
3. Aviles et al. Leuk. Lymphoma, 1998, 30, 5-6, p. 651-656
4. Gilbert, Cancer, 1998, 83, 6, p. 1205-13
5. Rutledge, Chin and Schepartz. Current Opinion in Chemical Biology, 2002, 6, p. 479-485
6. S. K. Narula, R. Coffman, eds. New cytokines as potential drugs, Birkhauser Verlag, Basel, 2000, 141 pp.
7. U.S. Pat. No. 5,231,081
8. Patent RU 2172322
9. Chernysh et al., Proceedings of National Academy of Science, 2002, 99, p. 12628-12632
10. Kourie, J. I. *Chem. Biol. Interact.*, 2001, 138, 1-26; Taylor, S. C., Green, K. N., Smith, I. F. & Peers, C. *Am. J. Physiol. Cell Physiol.*, 2001, 281, 1850-1857
11. Mabbott, N. A., Brown, K. L., Manson, J. & Bruce, M. E. *Immunology*, 1997, 92, p. 161-165
12. RU 2172322

BEST VARIANT OF THE INVENTION EMBODIMENT

Antitumoral and antiviral peptide comprising 13 aminoacids and corresponding to the structure of allostatin 1 is represented in the Example 1 as the best variant since it most completely discloses therapeutic efficacy of the declared peptide class according to the laboratory assessment. The peptide was synthesized by solid-phase synthesis technique using the automatic multi-channel synthesizer Multisyntech GmbH Witten and Fmoc-(N-[9-fluorenyl]methoxycarbonyl)-substituted amino acids. Purification of the synthesized peptide was carried out by technique of reversed-phase HPLC using Shimazu LC8 chromatograph equipped with 10 mm Chromasil C18 column. Purity of thus obtained peptide was also controlled by HPLC method (FIG. 1). Correctness of the synthesis is confirmed by MALDI-TOF mass-spectroscopy method using Finnigan TSQ 7000 device (FIG. 2). Mass of the peptide established experimentally corresponds to the calculated one, and deviations are within the range of measurement error.

INDUSTRIAL APPLICABILITY

Industrial applicability of the invention is confirmed by the results of laboratory studies and calculations that represented in the examples 1-6 and the Tables 4 and 5 mentioned below. These materials show that allostatin administration allows to suppress tumor cells proliferation and to eliminate them by the system of the organism immunological surveillance, which is a main goal of oncological diseases therapy and prophylaxis. Similarly, represented materials confirm the invention applicability to the therapy of viral infections by means of stimulation of antiviral immunity mechanisms. A method of declared peptides synthesis described in the application materials is available to enlargement in industrial conditions.

The invention claimed is:

1. A purified peptide comprising the amino acid sequence: His-Gly-Val-Ser-Gly-Trp-Gly-Gln-His-Gly-Thr-His-Gly (SEQ ID NO 1) or pharmaceutically acceptable salts, or ethers, or amides thereof.

2. The peptide of claim 1, having antiproliferative and cytotoxic activity.

3. The peptide of claim 1, having antitumoral activity.

4. The peptide of claim 1, having antiviral activity.

5. The peptide of claim 1, having interferonogenic activity.

6. A chemical compound having anti-proliferative, cytotoxic, antitumoral or antiviral activity, comprising the amino acid sequence His-Gly-Val-Ser-Gly-Trp-Gly-Gln-His-Gly-Thr-His-Gly (SEQ ID NO 1), wherein the chemical compound is not a natural peptide or protein.

7. A pharmaceutical composition comprising a peptide comprising the amino acid sequence His-Gly-Val-Ser-Gly-Trp-Gly -Gln-His-Gly-Thr-His-Gly (SEQ ID NO 1).

8. A pharmaceutical composition comprising the chemical compound of claim 6.

* * * * *

UNITED STATES PATENT AND TRADEMARK OFFICE
CERTIFICATE OF CORRECTION

PATENT NO.       : 8,372,406 B2                                                                      Page 1 of 1
APPLICATION NO. : 10/585715
DATED            : February 12, 2013
INVENTOR(S)      : Chernysh et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1617 days.

Signed and Sealed this
First Day of September, 2015

Michelle K. Lee
*Director of the United States Patent and Trademark Office*